US010363064B2

(12) United States Patent
Faria et al.

(10) Patent No.: US 10,363,064 B2
(45) Date of Patent: Jul. 30, 2019

(54) APPARATUS FOR PROVIDING ACCESS TO A BODY CAVITY OF A LIVING ANIMAL FOR A MEDICAL PROCEDURE

(71) Applicant: TITAN MEDICAL INC., Toronto (CA)

(72) Inventors: Leonard Faria, Swansea, MA (US); Joseph Gordon, Mansfield, MA (US); Rene Robert, East Greenwich, RI (US)

(73) Assignee: Titan Medical Inc., Toronto, Ontario (CA)

( * ) Notice: Subject to any disclaimer, the term of this patent is extended or adjusted under 35 U.S.C. 154(b) by 85 days.

(21) Appl. No.: 15/690,035

(22) Filed: Aug. 29, 2017

(65) Prior Publication Data

US 2019/0059935 A1 Feb. 28, 2019

(51) Int. Cl.
*A61B 17/02* (2006.01)
*A61B 17/34* (2006.01)
(Continued)

(52) U.S. Cl.
CPC ...... *A61B 17/3423* (2013.01); *A61B 17/0218* (2013.01); *A61B 17/34* (2013.01);
(Continued)

(58) Field of Classification Search
CPC . A61B 17/3423; A61B 17/0218; A61B 17/34; A61B 17/3431; A61B 17/3474;
(Continued)

(56) References Cited

U.S. PATENT DOCUMENTS 5,972,020 A 10/1999 Carpentier et al.
6,024,736 A * 2/2000 de la Torre ........ A61B 17/3423 128/898
(Continued)

FOREIGN PATENT DOCUMENTS

CA 2 680 915 3/2010
CA 2 701 866 10/2010
(Continued)

OTHER PUBLICATIONS

GelPOINT, Advanced Access Platforms, Applied Medical, www.appliedmedical.com/gelpoint (2017) in 6 pages.
(Continued)

*Primary Examiner* — Pedro Philogene
(74) *Attorney, Agent, or Firm* — Knobbe Martens Olson & Bear, LLP

(57) ABSTRACT

Method and apparatuses for providing access to a body cavity of a living animal through an access port inserted in an incision made in a wall of the body cavity are disclosed. In some embodiments, the apparatus includes a cap configured to attach to the access port, the cap including an opening configured to permit insertion of a medical instrument through the cap and access port into the body cavity, and a tubular sleeve including a distal end sealingly connected at the opening and extending outwardly therefrom, the sleeve including a proximal end configured to receive and provide a seal with the medical instrument when received. The apparatus also includes a closure disposed to temporarily seal the sleeve prior to insertion of the medical instrument through the opening in the cap.

9 Claims, 3 Drawing Sheets

(51) Int. Cl.
*A61M 13/00* (2006.01)
*A61B 46/10* (2016.01)
*A61B 90/40* (2016.01)

(52) U.S. Cl.
CPC ....... *A61B 17/3431* (2013.01); *A61B 17/3474* (2013.01); *A61B 46/10* (2016.02); *A61B 90/40* (2016.02); *A61B 2017/0225* (2013.01); *A61B 2017/347* (2013.01); *A61M 13/003* (2013.01)

(58) Field of Classification Search
CPC ...... A61B 2017/0225; A61B 2017/347; A61B 46/10; A61B 90/40; A61M 13/003
USPC ....... 600/104, 201, 203–206, 210, 227, 235, 600/245; 604/104, 27.34, 93.01, 99.03, 604/164.04, 164.08, 67.01, 167.02, 604/167.03, 174, 236, 264, 284; 606/191
See application file for complete search history.

(56) References Cited

U.S. PATENT DOCUMENTS 8,425,410 B2 * 4/2013 Murray .............. A61B 17/3423 600/203
8,485,970 B2 * 7/2013 Widenhouse ...... A61B 17/3462 600/201
2008/0033344 A1 2/2008 Mantell
2010/0312061 A1 * 12/2010 Hess ........................ A61B 1/32 600/201
2014/0235949 A1 * 8/2014 Smith ................ A61B 17/3462 600/201
2018/0049770 A1 2/2018 Zitnick et al.

FOREIGN PATENT DOCUMENTS

WO WO 2005/013832 2/2005
WO WO 2016/134452 9/2016

OTHER PUBLICATIONS

GelPort, Laparoscopic System, Applied Medical, www.appliedmedical.com/gelport (2015) in 2 pages.
SurgiSleeve Wound Protector with Retraction Ring, COVIDIEN (2015) in 3 pages.
Alexis, Wound Protectors/Retractors, Applied Medical, www.appliedmedical.com/alexis (2016) in 6 pages.
International Search Report & Written Opinion mailed by Canadian Intellectual Property Office dated May 4, 2016 in the corresponding PCT application No. PCT/CA2016/000054.

* cited by examiner

APPARATUS FOR PROVIDING ACCESS TO A BODY CAVITY OF A LIVING ANIMAL FOR A MEDICAL PROCEDURE

BACKGROUND

1. Field

This disclosure relates to apparatus used for surgical procedures and more particularly to providing access to a body cavity of a living animal for robotic and/or laparoscopic surgical instruments and equipment during the surgical procedure.

2. Description of Related Art

In robotic and laparoscopic surgery it is common to provide access to a body cavity of a patient through an access device. An incision is made by a surgeon in a wall of the body cavity and the access device is inserted into the incision to provide a sealed entry point for a surgical device such as a laparoscopic instrument. For robotic and laparoscopic surgery, the access device may be required to provide a seal to any instrument inserted into the body cavity through the access device. The seal maintains insufflation pressure in the body cavity during insertion and subsequent movement of the instrument. The access device further facilitates insufflation of the body cavity and the removal of smoke produced during electrocauterization of tissues within the body cavity, while maintaining the seal.

Commonly available access devices include surgical trocars such as those manufactured by Covidien PLC of Dublin, Ireland or by Stryker Corporation of Michigan, USA. Other types of access devices include wound protector/retractors such as the Alexis wound protector manufactured by Applied Medical Resources Corporation of Rancho Santa Margarita, Calif. and the SurgiSleeve™ wound protector manufactured by Covidien PLC. Wound retractors generally provide open access to the body cavity and are often used in conjunction with cap that covers the wound protector and provides a seal and a point of entry to the body cavity. Examples of available caps/sleeves that work with wound protectors are the GelPort laparoscopic system and the GelPOINT access platform, both manufactured by Applied Medical of California, USA.

SUMMARY

In accordance with one disclosed aspect there is provided an apparatus for providing access to a body cavity of a living animal through an access port inserted in an incision made in a wall of the body cavity.

The apparatus includes a cap configured to attach to the access port, the cap including an opening configured to permit insertion of a medical instrument through the cap and access port into the body cavity, and a tubular sleeve including a distal end sealingly connected at the opening and extending outwardly therefrom, the sleeve including a proximal end configured to receive and provide a seal with the medical instrument when received. The apparatus also includes a closure disposed to temporarily seal the sleeve prior to insertion of the medical instrument through the opening in the cap.

The sleeve may include a tapered sleeve including a larger opening at the distal end than the proximal end.

The sleeve may include a material that is at least partially transparent to permit observation of the medical instrument during insertion into the proximal end and through the opening in the cap.

The sleeve may include a flexible material.

The closure may include a releasable clamp disposed partway between the distal end and the proximal end and extending across the sleeve, the clamp being configured to engage and seal the sleeve to facilitate establishment of an insufflation pressure within the body cavity.

The closure may include a seal disposed proximate the proximal end of the sleeve and operably configured to be displaced by the medical instrument when inserted into the sleeve.

The proximal end of the sleeve may include a coupler including an o-ring configured to sealingly receive a bore of the medical instrument.

The access port may include an annular ring located outside the body cavity when inserted in the wall of the body cavity and the cap may be configured to snap over the annular ring.

At least one of the access port and the cap may include an inlet for receiving a fluid flow for insufflating the body cavity and a portion of the sleeve disposed between the closure and the distal end may be subjected to an insufflation pressure when the cap is received on the annular ring of the access port.

The opening may be configured to receive a first medical instrument and the cap may further include a second opening configured to receive a second medical instrument.

The access port may include one of a wound protector/retractor and a medical trocar.

In accordance with another disclosed aspect there is provided a method for providing access to a body cavity of a living animal. The method involves inserting an access port in an incision made in a wall of the body cavity, attaching a cap to the access port, the cap including an opening and a tubular sleeve including a distal end sealingly connected at the opening and extending outwardly therefrom, the sleeve being temporarily sealed by a closure to facilitate establishment of an insufflation pressure within the body cavity. The method also involves receiving a medical instrument through a proximal end of the sleeve, the proximal end being configured to provide a seal between the medical instrument and the proximal end of the sleeve when received, and causing the closure seal to be released to permit further insertion of the medical instrument through the opening in the cap and into the body cavity, the seal between the medical instrument and the proximal end of the sleeve being configured to contain the insufflation pressure within the body cavity.

Other aspects and features will become apparent to those ordinarily skilled in the art upon review of the following description of specific disclosed embodiments in conjunction with the accompanying figures.

BRIEF DESCRIPTION OF THE DRAWINGS

In drawings which illustrate disclosed embodiments.

DETAILED DESCRIPTION

Figure 1:
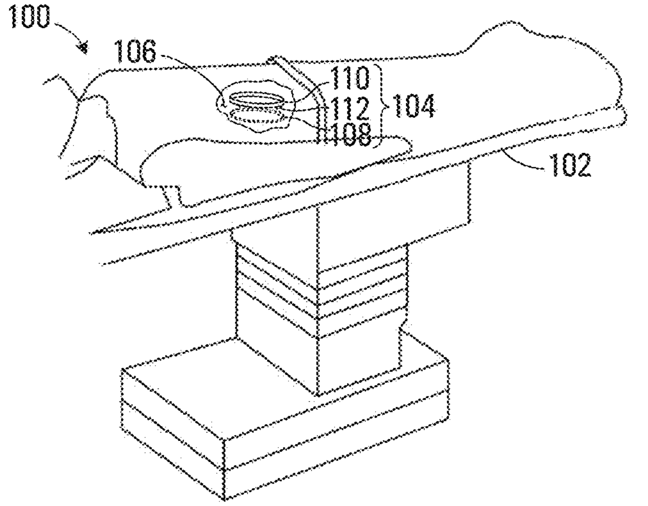
FIG. 1 is a depiction of a human patient undergoing a surgical procedure according to some embodiments.

Referring to FIG. 1, a human patient 100 is shown on a surgical table 102. The patient 100 has had an access port 104 inserted in the abdominal wall 106 to permit access to the patient's abdominal body cavity for a surgical procedure. In this embodiment the access port 104 (shown in hidden detail in FIG. 1) comprises a wound protector/retractor having a resilient internal ring 108 and a flexible or rigid external annular ring 110 joined by a sleeve 112. To insert the wound retractor, a surgeon makes an incision in the abdominal wall 106 and deforms the internal ring 108 to facilitate insertion through the incision. The internal ring 108 then retracts inside the body cavity and the internal and external ring 110 on either side of the incision hold the access port 104 in place within the abdominal wall 106. In other embodiments surgery may be performed in body cavities other than an abdominal body cavity of the patient 100 or the surgery may be performed on an animal.

The access port 104 may alternatively be implemented using a surgical trocar (not shown). Surgical trocars generally include a cannula that is either inserted directly through the incision or inserted through an access port such as a wound retractor. The cannula has a bore that permits insertion of instruments into the body cavity and may also include an insufflation inlet and an evacuation outlet. Whether received directly in the incision or through an access port 104, the trocar provides a point of entry to the body cavity, as in the case of the access port 104 shown in FIG. 1 and FIG. 2.

Figure 2:
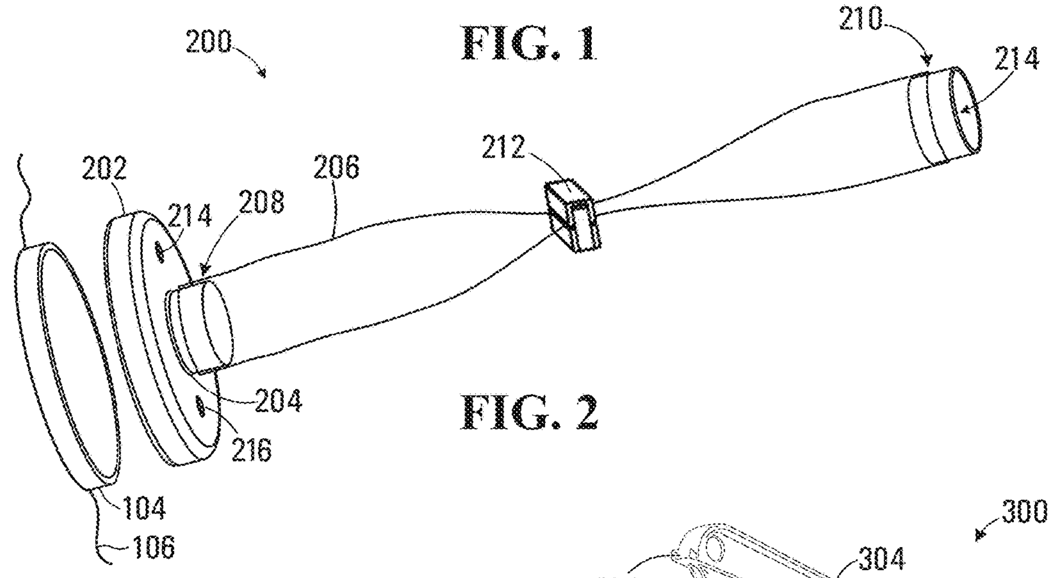
FIG. 2 is a perspective view of an access apparatus for providing access to the body cavity of the patient shown in FIG. 1 in accordance with some embodiments.

Referring to FIG. 2, one embodiment of an apparatus for providing access to the body cavity of the patient 100 through the access port 104 is shown generally at 200. The access apparatus 200 includes a cap 202 configured to attach to the access port 104. The cap 202 has an opening 204 configured to permit insertion of a medical instrument (not shown) through the cap and access port into the body cavity. The access apparatus 200 also includes a tubular sleeve 206 having a distal end 208 sealingly connected at the opening 204 and extending outwardly therefrom. The sleeve 206 has a proximal end 210 configured to receive and provide a seal with the medical instrument when received. The access apparatus 200 also includes a closure 212 disposed to temporarily seal the sleeve 206 prior to insertion of the medical instrument through the opening in the cap.

In the embodiment shown, the cap 202 is configured to sealingly engage the annular ring 110 of the access port 104 providing a sealed point of entry into the body cavity. In one embodiment the cap is operably configured to snap over the annular ring 110 to provide the seal.

The cap 202 includes an inlet port 214 for receiving a fluid flow from an insufflation line (not shown). Insufflation of the abdominal body cavity with a gas such as carbon dioxide distends the abdomen providing for entry and sufficient operating space for manipulation of surgical instruments during the surgical procedure. In this embodiment the cap 202 also includes an outlet port 216 for expelling fluid from the body cavity through an evacuation line (not shown). The expelled fluid may include smoke and other vapors produced by electrocauterization of tissue, for example. The inlet and outlet ports 214 and 216 may be implemented using standard fluid connections such as Luer taper connections or may be supplied with a length of tubing already attached. In other embodiments the inlet and outlet ports may be provided on the access port 104 (not shown).

In the embodiment shown the closure 212 is disposed partway between the distal end 208 and the proximal end 210 and extending across the sleeve 206. The closure 212 is configured to engage and seal the sleeve 206 to facilitate establishment of an insufflation pressure within the body cavity when the cap 202 is received on the annular ring 110 of the access port 104.

Figure 3:
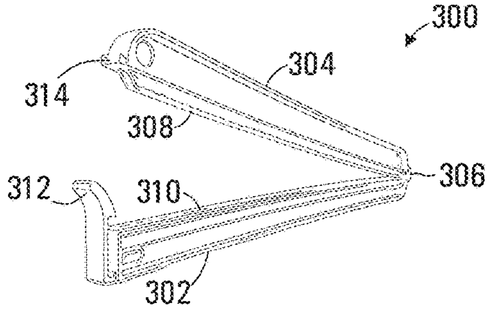
FIG. 3 is a perspective view of a closure used in the access apparatus shown in FIG. 2 according to some embodiments.

Referring to FIG. 3, a releasable clamp closure 300 in accordance with one embodiment of the disclosure is shown. The releasable clamp closure 300 is fabricated from a plastic material and is similarly configured to plastic closures commonly used for sealing food bags. The releasable clamp closure 300 includes a base portion 302 and an upper portion 304. The upper portion 304 is attached to the base via a living hinge 306.

The upper portion has a protruding rib 308 that is received within a recess 310 on the base portion 302 when closed. The base 302 also includes a resilient clasp 312, which is configured to receive and secure a protruding tang 314 on the upper portion 304 when the closure is closed over the tubular sleeve 206. The releasable clamp closure 300 shown in FIG. 3 is inexpensive and may be discarded after use.

Figure 4:
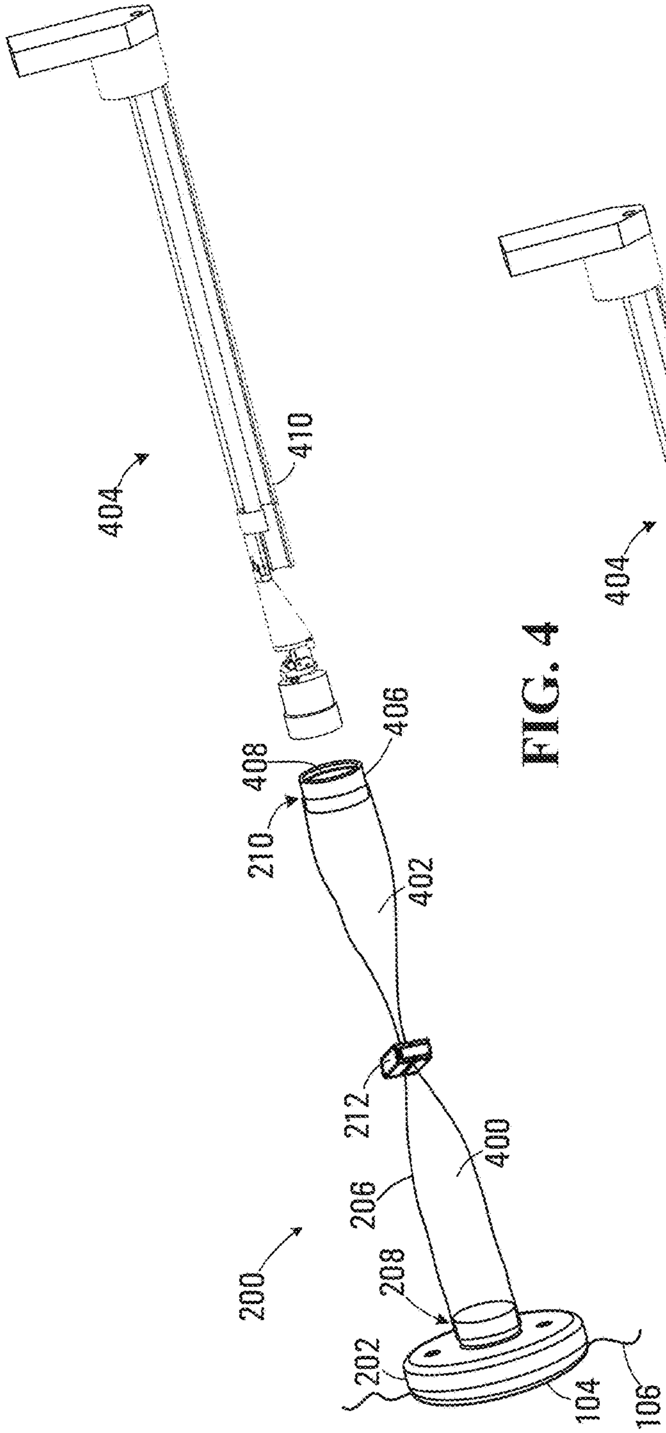
FIG. 4 is a perspective view of the access apparatus of FIG. 2 receiving a medical instrument according to some embodiments.

Referring to FIG. 4, the access apparatus 200 is shown with the cap 202 snapped on to the access port 104 and the closure 212 in place sealing the sleeve 206. The access port 104 has been inserted in the incision in the abdominal wall 106 and a distal portion 400 of the sleeve 206 will thus be subjected to the insufflation pressure. A proximate portion 402 of the sleeve 206 may be initially open to the environment and is disclosed to receive a medical instrument 404. In this embodiment the proximal end 210 of the access apparatus 200 includes a coupler 406 having an o-ring seal 408 disposed inside the coupler for sealingly receiving a bore 410 of the medical instrument 404. In this embodiment the medical instrument includes a camera that may be deployed in the body cavity to view the surgical site. In other embodiments the medical instrument may receive one or more tools for manipulating tissue during the surgery. The medical instrument may be a robotically controlled instrument that is controlled via an operator interface to perform surgical operations within the body cavity.

Figure 5:
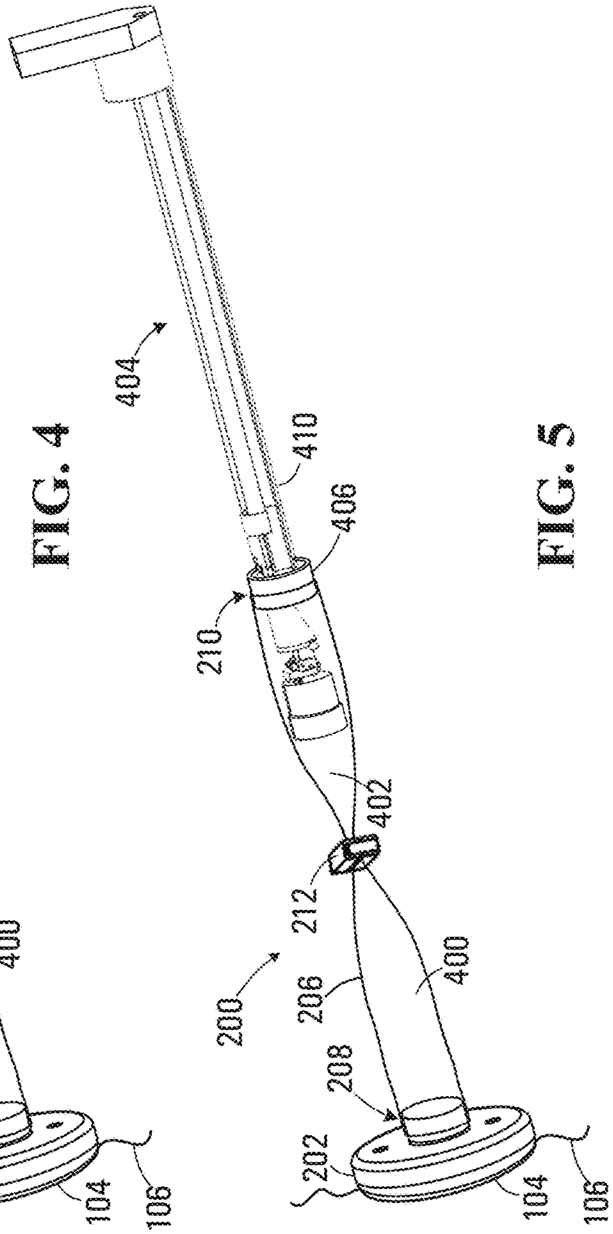
FIG. 5 is a further perspective view of the access apparatus of FIG. 2 receiving the medical instrument according to some embodiments.
Figure 6:
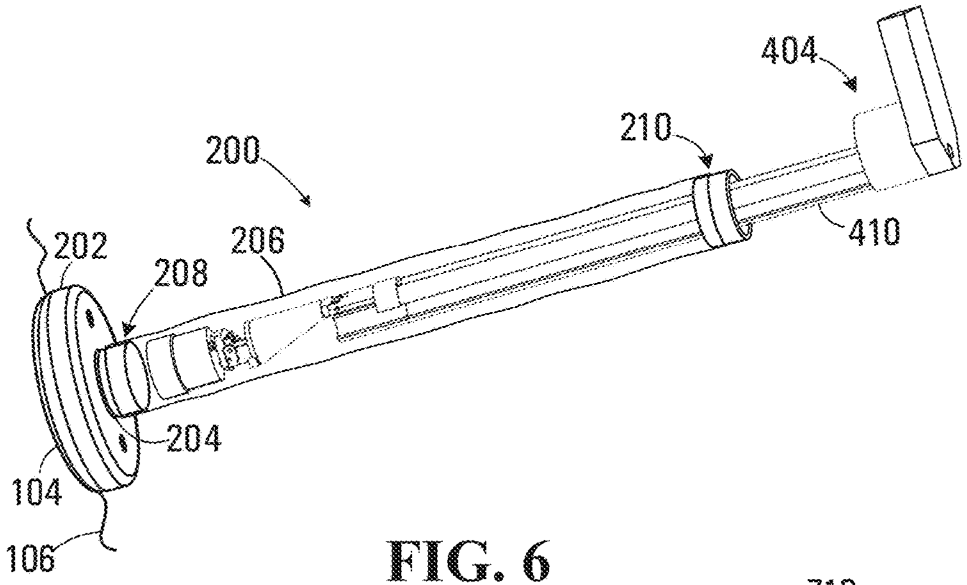
FIG. 6 is a perspective view of the access apparatus of FIG. 2 in which the medical instrument is received and a seal has been released according to some embodiments.

Referring to FIG. 5, the medical instrument 404 is shown having been inserted through the coupler 406 until the o-ring seal 408 engages the bore 410 of the medical instrument 404 to seal off the sleeve 206 from the environment. As this time the closure 212 may be removed from the sleeve 206. Referring to FIG. 6, the access apparatus 200 is shown with the closure 212 removed. A full length of the sleeve 206 between the distal end 208 and the proximal end 210 is subjected to the insufflation pressure and the medical instrument 404 is able to be inserted through the opening 204 in the cap 202 and into the body cavity without breaching the insufflation seal.

Figure 7:
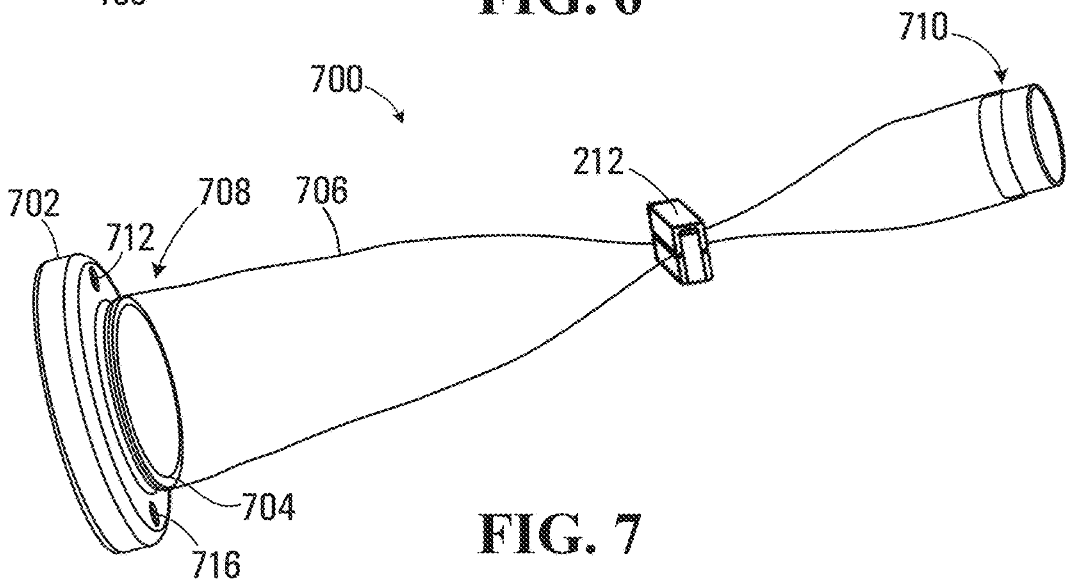
FIG. 7 is a perspective view of another embodiment of an access apparatus for providing access to the body cavity of the patient shown in FIG. 1 according to some embodiments.

Referring to FIG. 7, an alternative embodiment of an access apparatus is shown generally at 700. The access apparatus 700 includes a cap 702 having an enlarged opening 704 and a tapered sleeve 706 that has a larger opening at the distal end 708 than at a proximal end 710. The enlarged opening 704 facilitates maneuvering of the medical instrument once inserted into the tapered sleeve 706. The closure 212 is placed partway between the distal end 708 and the proximal end 710 where the sleeve 706 is somewhat narrower than at the distal end. The cap 702 includes an inlet port 712 and an outlet port 716 as described above in connection with the FIG. 2 embodiment.

Figure 8:
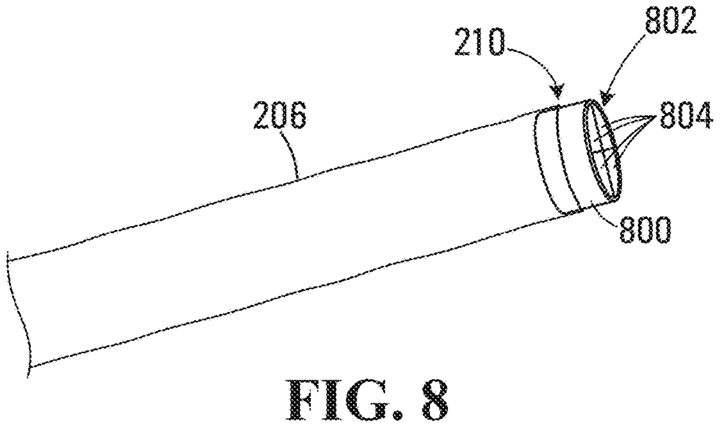
FIG. 8 is a perspective view of a portion of the access apparatus in accordance with some embodiments.

Referring to FIG. 8, a portion of the sleeve 206 of the access apparatus 200 shown in FIG. 2 is shown and includes an alternative embodiment of coupler 800 at the proximal end 210. In this embodiment the closure includes a displaceable seal 802 disposed in the coupler 800 and operably configured to be displaced by the medical instrument when inserted into the sleeve. The seal shown in FIG. 8 is commonly known as a duck-bill seal and includes flaps 804 that hold the insufflation pressure prior to insertion of the medical instrument but are easily displaced by the instrument when inserting through the coupler 800. In this embodiment the releasable clamp closure (212, 300) may be omitted since the displaceable seal 802 performs the sealing function. The displaceable seal 802 embodiment may also be applied to the access apparatus 700 shown in FIG. 7 having the tapered sleeve 706.

In other embodiments, the opening 204,704 in the respective caps 202 and 702 may be configured to receive a first medical instrument, and the cap may further include a second opening in the cap configured to receive a second medical instrument. In yet another embodiment, the sleeve 206 may be bifurcated partway along its length to provide a second opening at a proximal end to receive the second instrument.

While specific embodiments have been described and illustrated, such embodiments should be considered illustrative of the disclosure only and not as limiting the disclosure as construed in accordance with the accompanying claims.

What is claimed is:

1. An apparatus for providing access to a body cavity of a living animal through an access port inserted in an incision made in a wall of the body cavity, the apparatus comprising:

a cap configured to attach to the access port, the cap including an opening configured to permit insertion of a medical instrument through the cap and access port into the body cavity;

a tubular sleeve including a distal end sealingly connected at the opening and extending outwardly therefrom, the sleeve including a proximal end configured to receive and provide a seal with the medical instrument when received; and a closure disposed to temporarily seal the sleeve prior to insertion of the medical instrument through the opening in the cap, wherein the sleeve comprises a flexible material, and wherein the closure comprises a releasable clamp disposed partway between the distal end and the proximal end and extending across the sleeve, and wherein the clamp is configured to engage and seal the sleeve to facilitate establishment of an insufflation pressure within the body cavity.

2. The apparatus of claim 1 wherein the sleeve comprises a tapered sleeve including a larger opening at the distal end than the proximal end.

3. The apparatus of claim 1 wherein the sleeve comprises a material that is at least partially transparent to permit observation of the medical instrument during insertion into the proximal end and through the opening in the cap.

4. The apparatus of claim 1 wherein the closure comprises a seal disposed proximate the proximal end of the sleeve and operably configured to be displaced by the medical instrument when inserted into the sleeve.

5. The apparatus of claim 1 wherein the proximal end of the sleeve comprises a coupler including an O-ring configured to sealingly receive a bore of the medical instrument.

6. The apparatus of claim 1 wherein the access port comprises an annular ring located outside the body cavity when inserted in the wall of the body cavity and wherein the cap is configured to snap over the annular ring.

7. The apparatus of claim 6 wherein at least one of the access port and the cap comprises an inlet for receiving a fluid flow for insufflating the body cavity and wherein a portion of the sleeve disposed between the closure and the distal end is subjected to the insufflation pressure when the cap is received on the annular ring of the access port.

8. The apparatus of claim 1 wherein the opening is configured to receive a first medical instrument and further comprising a second opening in the cap configured to receive a second medical instrument.

9. The apparatus of claim 1 wherein the access port comprises one of a wound protector/retractor and a medical trocar.

* * * * *